(12) United States Patent
Makower et al.

(10) Patent No.: US 7,648,367 B1
(45) Date of Patent: Jan. 19, 2010

(54) ANATOMICAL MODELS AND METHODS FOR TRAINING AND DEMONSTRATION OF MEDICAL PROCEDURES

(75) Inventors: Joshua Makower, Los Altos, CA (US); John H. Morriss, Portola Valley, CA (US); Robert N. Wood, Indian Beach, NC (US); John Y. Chang, Mountain View, CA (US); Greg Miller, Livermore, CA (US)

(73) Assignee: Acclarent, Inc., Menlo Park, CA (US)

( * ) Notice: Subject to any disclaimer, the term of this patent is extended or adjusted under 35 U.S.C. 154(b) by 452 days.

(21) Appl. No.: 11/527,773

(22) Filed: Sep. 25, 2006

Related U.S. Application Data

(60) Provisional application No. 60/719,802, filed on Sep. 23, 2005.

(51) Int. Cl.
*G09B 23/28* (2006.01)

(52) U.S. Cl. .................................... 434/262; 434/267

(58) Field of Classification Search ................ 434/219, 434/262, 267
See application file for complete search history.

(56) References Cited

U.S. PATENT DOCUMENTS

| | | | |
|---|---|---|---|
| 6,503,087 B1 * | 1/2003 | Eggert et al. | 434/262 |
| 7,174,774 B2 * | 2/2007 | Pawar et al. | 73/73 |

* cited by examiner

*Primary Examiner*—Cameron Saadat
(74) *Attorney, Agent, or Firm*—Robert D. Buyan; Stout, Uxa, Buyan & Mullins

(57) ABSTRACT

Anatomical models representing one or more anatomical structures of a human or non-human animal and related methods for demonstrating, training, promotion and sale of medical, cosmetic and surgical products or procedures. A working device is inserted into the anatomical model and used to perform a simulated procedure, thereby causing an indicator apparatus (e.g., a removable business card) to become perceptibly altered. The indicator apparatus may then be removed and provided a potential user, consumer or purchaser of the medical, surgical or cosmetic product.

22 Claims, 4 Drawing Sheets

ANATOMICAL MODELS AND METHODS FOR TRAINING AND DEMONSTRATION OF MEDICAL PROCEDURES

RELATED APPLICATION

This patent application claims priority to U.S. Provisional Patent Application No. 60/719,802 entitled Anatomical Models and Methods for Training and Demonstration of Medical Procedures, filed on Sep. 23, 2005.

FIELD OF THE INVENTION

The present invention pertains generally to the fields of engineering, business and medicine and more particularly to anatomical model devices and related training, demonstration and business methods.

BACKGROUND OF THE INVENTION

In many cases, anatomical models are intended for visual observation only and are typically used for classroom demonstration, patient education and similar purposes. In other cases, anatomical models have been adapted for use in training surgeons to perform specific surgical or interventional procedures. The use of such anatomical models in surgical training allows the surgeon to practice at least some aspects of a particular procedure using the model rather than a cadaver, living animal or human patient.

One particular anatomical model that has been used for training surgeons in the performance of endoscopic sinus surgery is the SurgTrainer™ Human Nasal Model for Endonasal Surgery Training available from SurgTrainer, Ltd., 4-4-21, Kasuga, Tsukuba City, Ibaraki 305-0821 Japan. Also see, see, Yamauchi Y, Yamashita J, Mochimaru M, Fukui Y, Niikura M, Uno H, Yokoyama K, "Development of a Silicone Model for Endoscopic Sinus Surgery," proc CARS 99, p. 1039, 1999). This device generally includes a head-shaped housing into which various anatomical inserts may be interchangeably inserted and a soft plastic covering representing the skin and soft tissue structures of the patient's face. The interchangeable inserts represent various bone/sinus configurations representative of pathological conditions and, in at least some cases, are designed to be incised, drilled or cut by the surgeon undergoing training. This model is purported to be x-ray and CT compatible and may be used in conjunction with image guided surgical systems.

Recently, new catheter-based procedures have been developed by Acclarent, Inc. of Menlo Park, Calif. for the performance of less traumatic sinus and endonasal surgeries. These new procedures include, but are not limited to, uncinate-sparing Baloon Sinuplasty™ procedures and uncinate-sparing ethmoidectomy procedures using catheters, non-rigid instruments and advanced imaging techniques (Acclarent, Inc., Menlo Park, Calif.). Examples of these new devices, systems and methods are described in incorporated U.S. patent application Ser. Nos. 10/829,917 entitled Devices, Systems and Methods for Diagnosing and Treating Sinusitis and Other Disorders of the Ears, Nose and/or Throat; 10/944,270 entitled Apparatus and Methods for Dilating and Modifying Ostia of Paranasal Sinuses and Other Intranasal or Paranasal Structures; 11/116,118 entitled Methods and Devices for Performing Procedures Within the Ear, Nose, Throat and Paranasal Sinuses filed Apr. 26, 2005 and 11/150,847 filed Jun. 10, 2005, of which this application is a continuation-in-part. Baloon Sinuplasty™ procedures are performable using various types of guidance including but not limited to C-arm fluoroscopy, transnasal endoscopy, optical image guidance and/or electromagnetic image guidance. No commercially available anatomical models are known to have heretofore been adapted for demonstration, training or promotion of these Baloon Sinuplasty™ procedures or other endonasal or transnasal catheter-based procedures.

Accordingly, there remains a need in the art for the development of new anatomical models and related methods for training, demonstration, promotion and sale of medical and surgical products, including catheter-based endonasal and transnasal procedures.

SUMMARY OF THE INVENTION

The present invention generally provides devices that are useable for training and demonstrating various procedures, including medical, surgical, interventional, nursing, technical, veterinary, dental and other procedures carried out for purposes of treatment, diagnosis, hygiene, patient care, access, etc.

In accordance with the invention, there is provided a device that generally comprises: a) an anatomical model representing one or more anatomical structures of a human or non-human animal, b) an opening in the model through which a working device may be inserted and advanced to a desired procedure location and c) an indicator apparatus that provides an indication of when the working device has been used to cause some particular effect without causing substantial dismantling or destruction of the anatomical model. The indicator apparatus may indicate either a desired effect (e.g., the intended therapeutic or diagnostic effect of the working device) or an undesired effect (e.g., a complication, side effect, error, mistake or untoward effect) resulting from use of the working device.

Further in accordance with the invention, there are also provided methods for using anatomical models for demonstration, training, promotion or sales of a medical, surgical or cosmetic procedure (e.g., a therapeutic, diagnostic, surgical, interventional, nursing, technical, veterinary, dental or other procedure).

Further objects and aspects of the present invention will become apparent to those of skill in the art upon reading the detailed description, examples and claims set forth herebelow.

DETAILED DESCRIPTION AND EXAMPLES

The following detailed description and the accompanying drawings are intended to describe some, but not necessarily all, examples or embodiments of the invention. The contents of this detailed description do not limit the scope of the invention in any way.

Figure 1A:
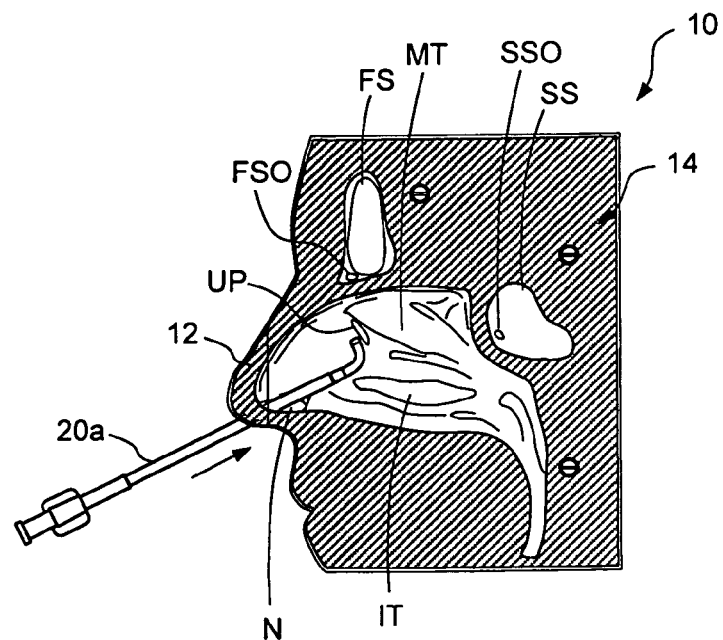
FIG. 1A is a left side view of a device of the present invention during insertion of a guide catheter.
Figure 1B:
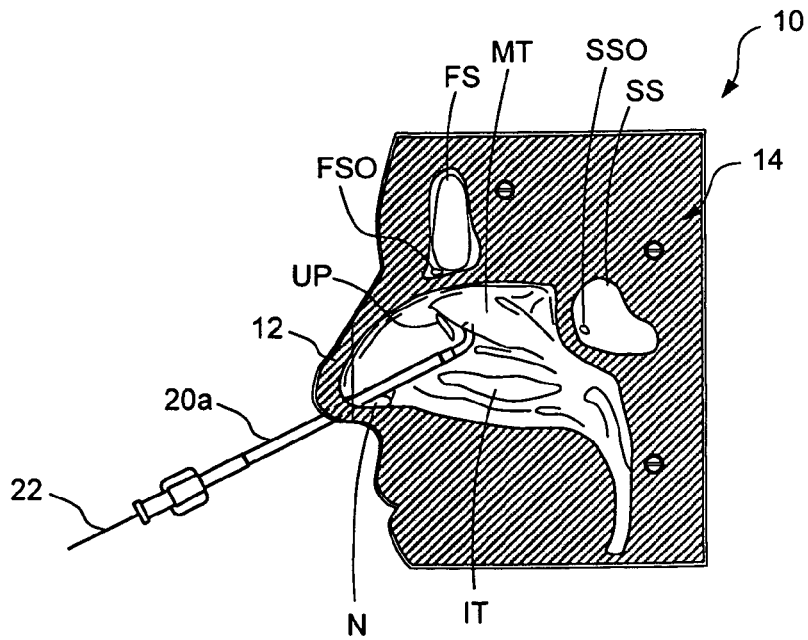
FIG. 1B is a left side view of the device of FIG. 1A with the guide catheter positioned with its distal end adjacent to the ostium of the maxillary paranasal sinus.
Figure 1C:
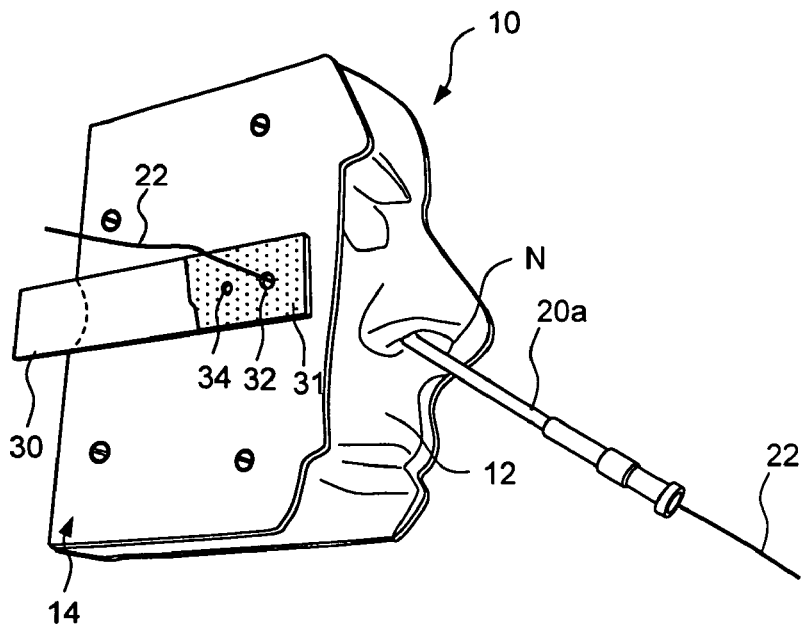
FIG. 1C is a right/front perspective view of the device of FIG. 1B with an indicator card attached and a guidewire having been advanced through the guide catheter, through the ostium of the maxillary sinus and through one opening formed in the indicator card.
Figure 1D:
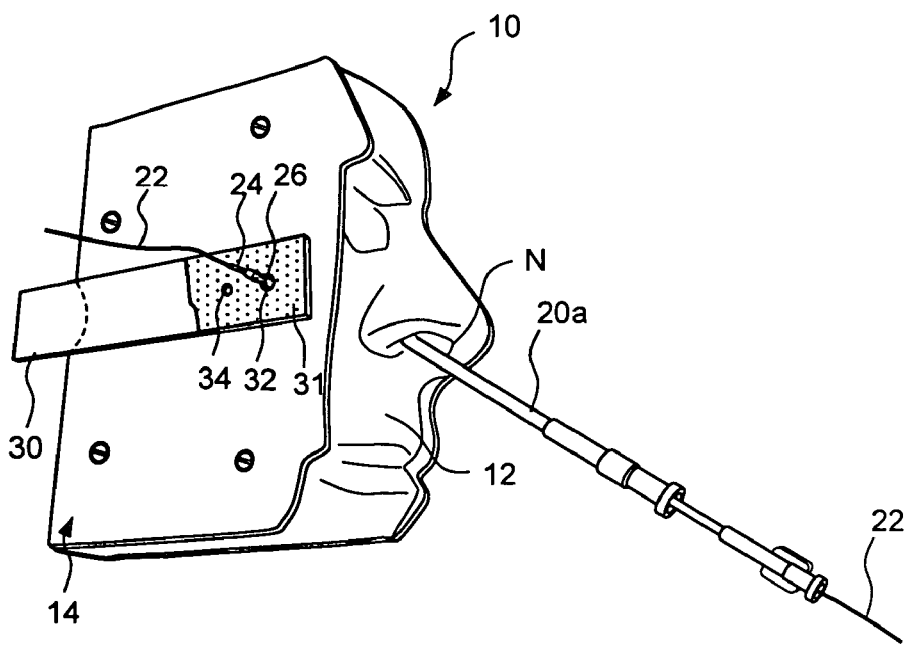
FIG. 1D is a right/front perspective view of the device of FIG. 1C with a balloon catheter advanced over the guidewire to a position where its balloon is located within the ostium of the maxillary paranasal sinus and extends through one opening formed in the indicator card.
Figure 1:
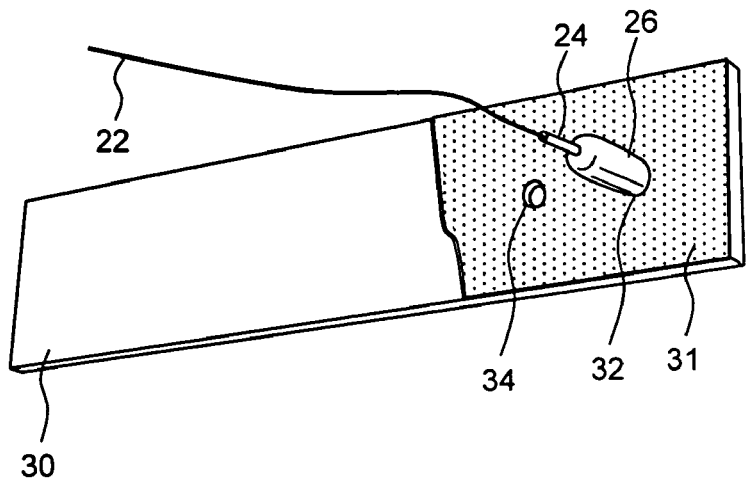
FIGS. 1E through 1G are enlarged views of the indicator card of the device of FIG. 1D, showing steps in a method for using the balloon to dilate the ostium of the paranasal sinus while, at the same time, enlarging one opening in the indicator card.
Figure 1:
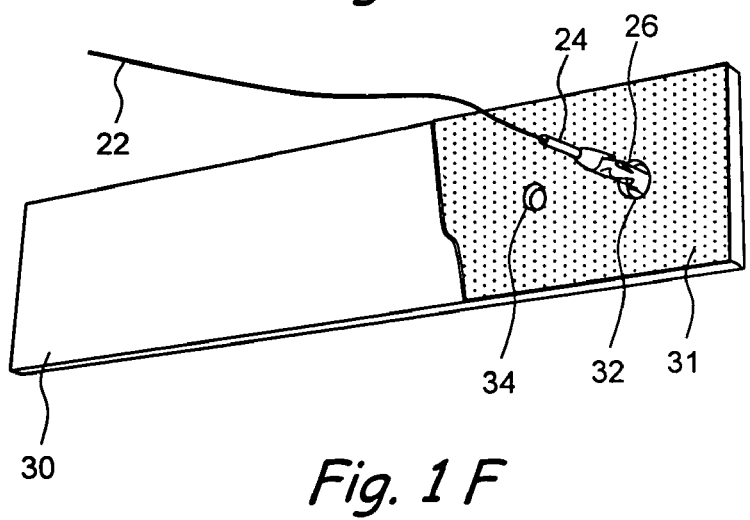
Figure 1:
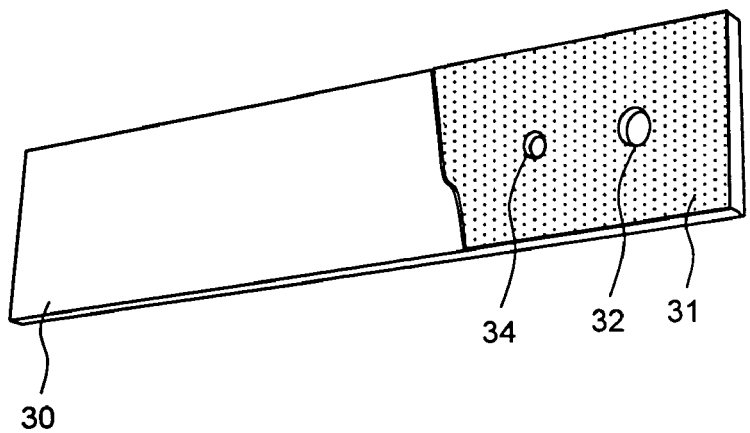

Certain examples of devices and methods of the present invention are shown in FIGS. 1A through 3 appended hereto. In these examples, the model device 10 comprises a plastic model 12 of a portion of a human head including certain structures of the nose and nasal cavity. In particular, the following is a key to reference letters used to denote specific anatomical structures on the accompanying figures:

N Nares
FS Frontal Sinus
SS Sphenoid Sinus
MSO Maxillary Sinus Ostium
SSO Sphenoid Sinus Ostium
FSO Frontal Sinus Ostium
IT Inferior Turbinate
MT Medial Turbinate
UP Uncinate Process Internal anatomical structures are mainly visible on one side of the model 12 as seen in FIGS. 1A, 1B, 2 and 3. The other side of the model 12 is substantially flat and has an opening representing the maxillary sinus ostium MSO, as seen in FIGS. 1C and 1D. Optionally, panels 14 of clear plastic or other suitable material may be affixed over one or both sides of the model 12 as seen in a number of the drawings.

The model device 10 shown in this example includes one or more indicator apparatus 30, such as a card, that may be inserted into or attached to the device 10. This indicator apparatus 30 provides an indication of when a working device (for example a balloon catheter 24) has been used to cause a particular effect (for example, dilation of an opening 32 formed in the indicator apparatus 30) without requiring substantial dismantling or destruction of the anatomical model. In this example, the indicator apparatus 30 comprises a card that has an effect indicating region 31 formed of plastic foam, a test opening 32 and a reference opening 34 formed therein. Initially the test opening 32 and reference opening 34 are the same size. However, as explained more fully herebelow, when a working device (for example a balloon catheter 24) has been successfully used in a manner that would dilate the ostium of a paranasal sinus, the test opening 32 becomes enlarged. The indicator apparatus 30 may then be removed from the model 12 and the size of the enlarged test opening 32 may be compared to the original size of the reference opening 34.

FIGS. 1A-1E show one example of a method in which a model device 10 of this invention is used to demonstrate, promote or provide training in the use of a guide catheter 20a, guidewire 22 and balloon catheter 24 useable to dilate a maxillary sinus ostium MSO. The indicator apparatus 30 is inserted between the flat side of the model 12 and a clear plastic panel 14 that has been attached to that side of the model 12. A hole in the clear plastic panel 14 is aligned with the maxillary sinus ostium MSO. The test opening 32 of the indicator apparatus is positioned between the maxillary sinus ostium MSO and the aligned hole in the panel 14. A guide catheter 20a having a curved tip is initially inserted through the nares N, advanced around the uncinate process UP and adjacent to the medial turbinate MT and positioned such that its distal end is adjacent to the maxillary sinus ostium MSO. A guidewire 22 is then advanced through the guide catheter 20a and through the maxillary sinus ostium MSO, through the test opening 32 and through the aligned opening in the panel 14 such that the guidewire 22 protrudes outwardly from the side of the device 10 (see FIG. 1C). Thereafter, a balloon catheter 24 having a balloon 26 in a deflated state is advanced over the guidewire 22 to a position where the deflated balloon 26 is situated within the maxillary sinus ostium MSO and test opening 32 of the indicator apparatus (see FIG. 1D). Thereafter, the balloon 26 is inflated in a manner that would dilate the maxillary sinus ostium MSO of a patient (see FIG. 1E). This causes discernible enlargement of the test opening 32 of the indicator apparatus. Thereafter, the balloon 26 is deflated (see FIG. 1F) and the guide catheter 20a, balloon catheter 24 and guidewire are removed (see FIG. 1G), leaving the test opening 32 discernibly larger than the reference opening 34, thereby indicating that the treatment would have successfully dilated the maxillary sinus ostium of a human patient. The indicator apparatus may be removed from the device 10 without requiring substantial dismantling and/or destruction of the model 12 and another indicator apparatus 30 may then be inserted and the procedure repeated.

It will be appreciated that this device 10 may also be used to provide demonstration or training of other procedures wherein devices are inserted into other paranasal sinuses. In this regard, FIGS. 2 and 3 show examples of methods wherein this model device 10 is used to provide demonstration or training of methods wherein guidewires and/or working devices are inserted into sphenoid sinuses SS, sphenoid sinus ostia SSO, frontal sinuses FS or frontal sinus ostia FSO.

Figure 2:
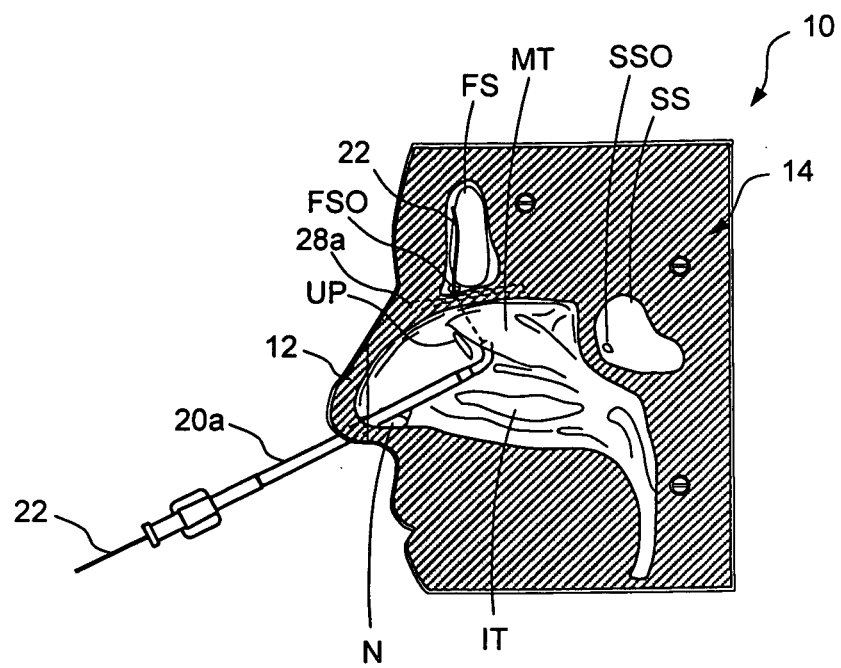
FIG. 2 is a left side view of a device of the present invention with a guide catheter and guidewire being used to access the frontal sinus.

Specifically referring to FIG. 2, a curved guide catheter 20a may be advanced through the nares N, navigated around the uncinate process UN and placed in a position where its distal tip is adjacent to the frontal sinus ostium FSO. Thereafter, a guidewire 22 may be advanced through the guide catheter 20a and into the frontal sinus FS. This provides demonstration or training of minimally traumatic catheter based access of the frontal sinus FS. Optionally, as shown in FIG. 2, a slot 28a may be provided for insertion of an appropriately sized and configured indicator apparatus 30 into position adjacent to the frontal sinus ostium FSO and a balloon catheter 24 or other working device may be advanced over the guidewire 22 and used in a manner that would dilate or modify the frontal sinus ostium FSO in a human patient, thereby resulting in a discernible change in that indicator apparatus 30. That indicator apparatus 30 may ten be removed from slot 28a without requiring substantial dismantling or destruction of the model 12 and another indicator apparatus 30 may then be inserted and the procedure repeated.

Figure 3:
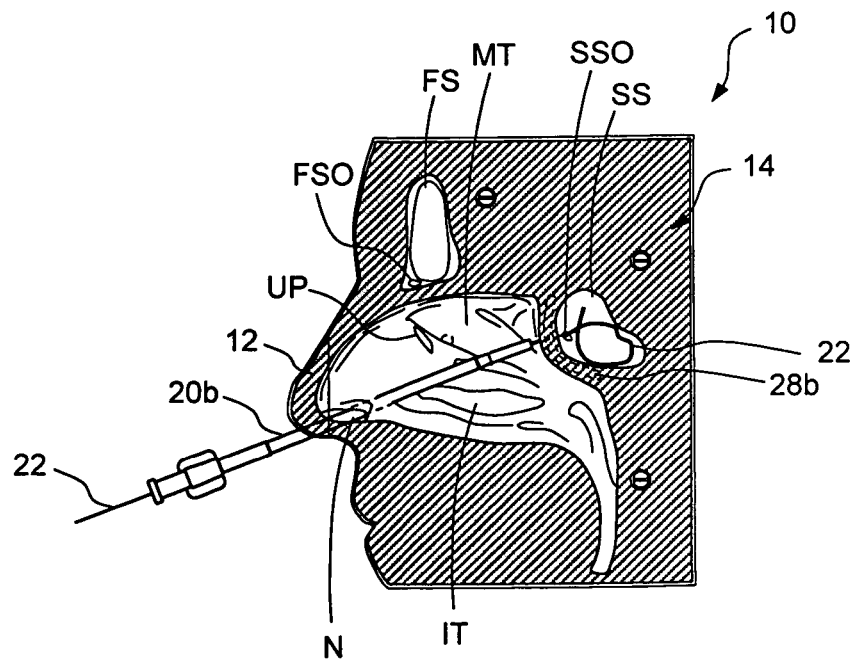
FIG. 3 is a left side view of a device of the present invention with a guide catheter and guidewire being used to access the sphenoid sinus.

Specifically referring to FIG. 3, a straight guide catheter 20b may be advanced through the nares N, navigated past the medial turbinate and placed in a position where its distal tip is adjacent to the sphenoid sinus ostium SSO. Thereafter a guidewire 22 may be advanced through the guide catheter 20b and into the sphenoid sinus SS. This provides demonstration or training of minimally traumatic catheter based access of the sphenoid sinus SS. Optionally, as shown in FIG. 3, a slot 28b may be provided for insertion of an appropriately sized and configured indicator apparatus 30 into position adjacent to the sphenoid sinus ostium SSO and a balloon catheter 24 or other working device may be advanced over the guidewire 22 and used in a manner that would dilate or modify the sphenoid sinus ostium SSO in a human patient, thereby resulting in a discernible change in that indicator apparatus 30. That indicator apparatus 30 may be removed from slot 28b without requiring substantial dismantling or destruction of the model 12 and another indicator apparatus 30 may then be inserted and the procedure repeated.

It is to be appreciated that, while these examples are specific to accessing of paranasal sinuses and dilation of the natural ostia or other openings in paranasal sinus, the present invention may be used to provide demonstration or training of a wide variety of other procedures in the ear, nose and throat or elsewhere in the body of a human or non-human animal subject. Moreover, the particular effect indicated by the indicator apparatus 30 is not limited to just dilator or enlargement of an opening, but may include any discernible effect of any working device, including but not limited to causing any anatomical structure to become cut, pierced, penetrated, ablated, removed, excised, irradiated, wetted, trimmed, remodeled, reshaped, severed or otherwise modified.

Additionally, one or more portions of the model 12 may be removable and/or malleable and/or reconfigurable and/or replaceable to represent different anatomical structures, variations or conditions such as: normal anatomical variations, disease states or disorders, effects of pathology, pathogenic or etiological stages of a disorder, congenital malformations, anatomical anomalies, effects of prior surgery, effects of prior therapy, effects of drug administration, effects of aging or maturation, etc. For applications in the ear, nose and throat area, portion(s) of the model 12 may be removable and/or malleable and/or reconfigurable and/or replaceable to represent various ear, nose or throat structures, variations or disorders including but not limited to: ostia of paranasal sinuses, ethmoid cells, various types of frontal ethmoid cells (e.g., type 1, 2, 3, 4), Onodi cells, Haller cells, septations in frontal, maxillary, sphenoid sinuses, variations in size and shape of paranasal sinuses, the effects of prior sinus or ENT surgery, prior ethmoidectomy, prior uncinectomy, prior frontal sinusotomy, mucoceles, polyps, papillomas, carcinoma, inflamed mucosa, osteoneogenesis, scarring/narrowing/adhesions, deviated septum, concha bullosa, paradoxical turbinates, agger nasi cells, variations in size of turbinates, uncinate, etc., superior and supreme turbinates, the optic nerve, the lachrymal duct, the anterior ethmoid artery, retrobullar recesses, suprabullar recesses, inferior turbinates and normal or atresic Eustachian tubes. It is to be understood, however, that the applicability of this device is not limited to the field of otorhinolaryngology. In fact the devices and method of this invention may be used in many applications including medical, surgical, interventional, nursing, technical, veterinary, dental and other procedures carried out for purposes of treatment, diagnosis, hygiene, patient care, access, etc. in many areas of the body.

Any portions of the model 12 that are removable or replaceable may be inserted into or attached to the model 12 by any suitable means including but not limited to: slots or cavities that fit entire detachable element; slots or cavities that fit a locking portion of the detachable element; magnetic attachments; hook and loop type fasteners (e.g. Velcro™); screw type fasteners; adhesives (e.g., temporary adhesives such as those used on Post-it™ Notes); suction cups; etc.

It is to be appreciated that the invention has been described hereabove with reference to certain examples or embodiments of the invention but that various additions, deletions, alterations and modifications may be made to these examples and embodiments without departing from the intended spirit and scope of the invention. For example, any element or attribute of one embodiment or example may be incorporated into or used with another embodiment or example, unless otherwise specified or unless to do so would render the embodiment or example unsuitable for its intended use. Also, where the steps of a method or process are described or listed in a specific order, the order of any such steps may be changed unless otherwise specified or unless to do so would render the embodiment or example unsuitable for its intended use. All reasonable additions, deletions, modifications and alterations are to be considered equivalents of the described examples and embodiments and are to be included within the scope of the following claims.

What is claimed is:

1. A device comprising:
    an anatomical model representing one or more anatomical structures of a human or non-human animal;
    an opening in the model through which a working device may be inserted and advanced to a desired procedure location and used to enlarge or dilate an opening, channel, lumen, indentation, gap or other structure; and
    an indicator apparatus that provides an indication of when the working device has been used to effect a desired enlargement or dilation of an opening, channel, lumen, indentation, gap or other structure, said indication being discernible without requiring substantial dismantling or destruction of the anatomical model;
    wherein the indicator apparatus comprises a removable card member which has, formed therein, an opening, channel, lumen, indentation, gap or other structure which becomes enlarged or dilated when the working device has been used to cause enlargement or dilation of that opening, channel, lumen, indentation, gap or other structure.

2. A device according to claim 1 wherein the opening in the model through which a working device may be inserted represents a natural body opening.

3. A device according to claim 1 wherein the opening in the model through which a working device may be inserted is shaped and located to represent a body opening of a human or animal subject, said body opening being selected from the group consisting of: the mouth, nose, ear, anus, urethra, vagina and exocrine duct.

4. A device according to claim 1 wherein the opening in the model through which a working device may be inserted represents a man-made or non-naturally occurring body opening.

5. A device according to claim 1 wherein the opening in the model through which a working device may be inserted is shaped and located to represent an opening that has been created in the body of a human or animal subject, said opening being selected from the group consisting of: incision, puncture tract, port, opening resulting from pathology and opening resulting from congenital deformity.

6. A device according to claim 1 wherein the removable card member is positionable on or in the anatomical model before attempting performance of a desired procedure and subsequently removable from the anatomical model after attempting performance of the desired procedure.

7. A device according to claim 6 wherein the removable card member is formed of at least one material selected from the group consisting of: cardboard, plastic, foamed plastic, paper, metal and glass.

8. A device according to claim 6 wherein the removable card member has a name or promotional information thereon.

9. A system comprising a device according to claim 1 further in combination with a working device that is insertable through the opening in the model, the working device having a working part that is useable to enlarge or dilate the opening, channel, lumen, indentation, gap or other structure formed in the removable card member.

10. A system according to claim 9 wherein the working device comprises a balloon catheter and wherein the working part comprises a balloon.

11. A device according to claim 1 further comprising a reference region in the removable card member for comparison to the opening, channel, lumen, indentation, gap or other structure.

12. A device according to claim 1 wherein the model is constructed to represent one or more anatomical structures within the ear, nose or throat.

13. A device according to claim 12 wherein the opening, channel, lumen, indentation, gap or other structure formed in the removable card member represents an opening into a paranasal sinus.

14. A device or system according to claims 1 wherein one or more portion(s) of the model is/are removable and/or malleable and/or reconfigurable and/or replaceable to represent different anatomical structures, variations or conditions.

15. A system comprising a device according to claim 14 in combination with one or more replacement parts that may be used to replace a removed portion of the model.

16. A system according to claim 15 wherein the one or more replacement parts are removable and/or malleable and/or reconfigurable and/or replaceable to represent structures, variations or conditions selected from: a) normal anatomical variations, b) disease states or disorders, c) effects of pathology, d) etiological stages of pathology, e) congenital malformations, f) anatomical anomalies, g) effects of prior surgery, h) effects of prior therapy, i) effects of drug administration, j) effects of aging or maturation, etc.

17. A system according to claim 16 wherein the model represents one or more anatomical structures within the ear, nose or throat and wherein the one or more replacement parts are removable and/or malleable and/or reconfigurable and/or replaceable to represent structures, variations or conditions selected from: a) ostia of paranasal sinuses, b) ethmoid cells, c) various types of frontal ethmoid cells, d) Onodi cells, e) Haller cells, f) septations in frontal, maxillary, sphenoid sinuses, g) variations in size and shape of paranasal sinuses, h) the effects of prior sinus or ENT surgery, I) prior ethmoidectomy, j) prior uncinectomy, k) prior frontal sinusotomy, l) mucoceles, m) polyps, n) papillomas, o) carcinoma, p) inflamed mucosa, q) osteoneogenesis, r) scarring/narrowing/adhesions, s) deviated septum, t) concha bullosa, u) paradoxical turbinates, v) agger nasi cells, w) variations in size of turbinates, uncinate, etc., x) superior and supreme turbinates, y) optic nerve, z) lachrymal duct, aa) anterior ethmoid artery, bb) retrobullar recesses, cc) suprabullar recesses, dd) inferior turbinates and ee) normal or atresic Eustachian tubes.

18. A system according to claim 15 wherein the one or more replacement parts are detachably attachable to the model by way of one or more detachable attachment means selected from the group consisting of: slots or cavities that fit a locking portion of the detachable element; magnetic attachments; hook and loop type fasteners; screw type fasteners; adhesives and suction cups.

19. A method for distributing promotional or business information, said method comprising the steps of:
   A) positioning, on or in an anatomical model, a removable card member having promotional or business information thereon;
   B) using a medical, surgical or cosmetic product to perform a simulated procedure on or in the anatomical model in a manner that perceptibly affects the removable card member; and
   C) removing the removable card member and providing it to a prospective user, consumer or purchaser of the medical, surgical or cosmetic product.

20. A method according to claim 19 wherein an opening is formed in the removable card member and wherein the simulated procedure causes the opening to become enlarged.

21. A method according to claim 20 wherein the removable card member further includes a reference opening for comparison to the enlarged opening.

22. A method according to claim 19 wherein the promotional or business information comprises name of a developer of or commercial source for the medical, surgical or cosmetic product.

\* \* \* \* \*

UNITED STATES PATENT AND TRADEMARK OFFICE
CERTIFICATE OF CORRECTION

PATENT NO. : 7,648,367 B1　　　　　　　　　　　　　　　　　　　　　　　　Page 1 of 1
APPLICATION NO. : 11/527773
DATED : January 19, 2010
INVENTOR(S) : Makower et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 568 days.

Signed and Sealed this

Twenty-eighth Day of December, 2010

David J. Kappos
*Director of the United States Patent and Trademark Office*